US012765761B2

(12) United States Patent
Ro

(10) Patent No.: US 12,765,761 B2
(45) Date of Patent: Oct. 20, 2026

(54) METHOD AND DEVICE FOR PROCESSING SCAN IMAGE OF THREE-DIMENSIONAL SCANNER

(71) Applicant: MEDIT CORP., Seoul (KR)

(72) Inventor: Jongcheol Ro, Seoul (KR)

(73) Assignee: MEDIT CORP., Seoul (KR)

( * ) Notice: Subject to any disclaimer, the term of this patent is extended or adjusted under 35 U.S.C. 154(b) by 341 days.

(21) Appl. No.: 18/565,385

(22) PCT Filed: May 25, 2022

(86) PCT No.: PCT/KR2022/007420
§ 371 (c)(1),
(2) Date: Jul. 17, 2024

(87) PCT Pub. No.: WO2022/255720
PCT Pub. Date: Dec. 8, 2022

(65) Prior Publication Data

US 2024/0407637 A1 Dec. 12, 2024

(30) Foreign Application Priority Data

May 31, 2021 (KR) ........................ 10-2021-0069828

(51) Int. Cl.
*A61B 1/24* (2006.01)
*A61B 1/00* (2006.01)

(52) U.S. Cl.
CPC .......... *A61B 1/24* (2013.01); *A61B 1/000095* (2022.02); *A61B 1/0004* (2022.02); *A61B 1/00045* (2013.01)

(58) Field of Classification Search
CPC ........... A61C 9/00; A61B 5/00; A61B 1/0004; A61B 1/00172; A61B 1/00194;
(Continued)

(56) References Cited

U.S. PATENT DOCUMENTS

2016/0256035 A1 9/2016 Kopelman et al.
2019/0269485 A1* 9/2019 Elbaz .................. A61C 9/0053
(Continued)

FOREIGN PATENT DOCUMENTS

JP 2016-174903 A 10/2016
JP 2019-166246 A 10/2019
(Continued)

OTHER PUBLICATIONS

Daly S, Seong J, Parkinson C, Newcombe R, Claydon N, West N. A proof of concept study to confirm the suitability of an intra oral scanner to record oral images for the non-invasive assessment of gingival inflammation. Journal of dentistry. Feb. 1, 2021;105:103579.*
(Continued)

*Primary Examiner* — Phu K Nguyen
(74) *Attorney, Agent, or Firm* — Sughrue Mion, PLLC

(57) ABSTRACT

Methods and apparatus for recording a process of constructing a three-dimensional image model based on information acquired from a three-dimensional scanner are provided. An electronic device according to the present disclosure comprises: a communication circuit communicatively connected to a three-dimensional scanner; an input device; a display; and at least one processor, wherein the at least one processor is configured to: generate a three-dimensional image of a shape of an oral cavity, based on an image acquired from the three-dimensional scanner; display, on the display, a screen comprising a first region in which at least the three-dimensional image is displayed; receive a user input for selectively recording a predetermined region of the screen; and generate a video image by recording a region of the screen corresponding to the user input in response to the user input, and wherein the recorded region comprises a portion of the first region.

21 Claims, 15 Drawing Sheets

(58) Field of Classification Search
CPC .......... A61B 1/00045; A61B 1/000095; A61B 1/0005; A61B 1/24; G06T 17/00
USPC .......................................................... 345/418
See application file for complete search history.

(56) References Cited

U.S. PATENT DOCUMENTS

| | | | | |
|---|---|---|---|---|
| 2020/0160947 | A1* | 5/2020 | Rasovsky | H04L 9/3247 |
| 2021/0045701 | A1* | 2/2021 | Unklesbay | A61B 6/51 |
| 2021/0264600 | A1 | 8/2021 | Jellinggaard et al. | |
| 2022/0101618 | A1* | 3/2022 | Reynard | G06T 7/30 |
| 2022/0122264 | A1* | 4/2022 | Reynard | A61B 6/51 |
| 2022/0133445 | A1* | 5/2022 | Kucharczyk | A61C 9/006 433/29 |
| 2024/0189065 | A1* | 6/2024 | Schnabel | G16H 30/40 |
| 2024/0407637 | A1* | 12/2024 | Ro | A61C 9/00 |

FOREIGN PATENT DOCUMENTS

| | | | |
|---|---|---|---|
| KR | 10-1181977 | B1 | 9/2012 |
| KR | 10-2019-0084344 | A | 7/2019 |
| KR | 10-2020-0068992 | A | 6/2020 |
| KR | 10-2021-0022691 | A | 3/2021 |
| WO | 2020/185527 | A1 | 9/2020 |

OTHER PUBLICATIONS

Kravitz ND, Groth CH, Jones PE, Graham JW, Redmond WR. Intraoral digital scanners. J Clin Orthod. Jun. 1, 2014;48(6):337-47.*

International Search Report for PCT/KR2022/007420 dated Aug. 29, 2022 [PCT/ISA/210].

Korean Office Action for 10-2021-0069828 dated May 31, 2021.

* cited by examiner

METHOD AND DEVICE FOR PROCESSING SCAN IMAGE OF THREE-DIMENSIONAL SCANNER

CROSS REFERENCE TO RELATED APPLICATIONS

This application is a National Stage of International Application No. PCT/KR2022/007420 filed May 25, 2022, claiming priority based on Korean Patent Application No. 10-2021-0069828 filed May 31, 2021, the entire disclosures of which are incorporated herein by reference.

TECHNICAL FIELD

The present disclosure relates to a method and a device for processing a scan image from a three-dimensional scanner. Specifically, the disclosure relates to a method and a device for recording a process of constructing a three-dimensional image model based on information acquired from a three-dimensional oral scanner.

BACKGROUND

An oral scanner is an optical device inserted into a patient's oral cavity to acquire a three-dimensional image of the oral cavity by scanning teeth.

The oral scanner scans an inner shape of the oral cavity into multiple 2D images, which are converted into a three-dimensional image model through a predetermined computational process. The scanned images or the converted three-dimensional images may be displayed on a display of an electronic device coupled to the oral scanner so that a user (e.g., a dentist or a dental hygienist) operating the oral scanner can view the images in real time.

The acquired 3D image model may be provided to a dental laboratory for fabrication of an artificial structure, an artificial tooth, or the like required for treatment. In this case, to understand how the three-dimensional image was formed through a scanning process, it may be necessary to record the user's scanning process, i.e., the process of forming the three-dimensional image, and provide the recorded scanning process to the dental laboratory. In addition, the scanning process shown on the display may be provided to an oral scanner manufacturer, and used as a reference for improving the performance of the oral scanner.

However, capturing and recording a screen displayed on the display of an electronic device may be a significant burden on a processor of the electronic device, and thus recording an unnecessary screen region may adversely affect the computational operation of the electronic device that converts scanned images into a three-dimensional image.

In addition, when an unnecessary screen region is recorded, a video file in which the recorded image is stored may also be large, causing inconvenience when delivering the video file to the dental laboratory.

On the other hand, when a screen region to be recorded is too narrow, the disadvantage that necessary information is not properly recorded may occur.

SUMMARY

The present disclosure is to solve the above-described problems of the prior art, and enables configuring a screen region to be recorded when recording a scanning process of a three-dimensional scanner displayed on a display screen.

As one aspect of the present disclosure, an electronic device for processing a scan image of a three-dimensional scanner may be suggested. An electronic device according to an aspect of the present disclosure comprises: a communication circuit communicatively connected to a three-dimensional scanner; an input device; a display; and at least one processor, wherein the at least one processor is configured to: generate a three-dimensional image of a shape of an oral cavity, based on an image acquired from the three-dimensional scanner via the communication circuit; display, on the display, a screen comprising a first region in which at least the three-dimensional image is displayed; receive a user input for selectively recording a predetermined region of the screen; and generate a video image by recording a region of the screen corresponding to the user input in response to the user input, and wherein the recorded region comprises a portion of the first region.

As one aspect of the present disclosure, a method for processing a scan image of a three-dimensional scanner may be suggested. A method according to an aspect of the present disclosure comprises generating a three-dimensional image of a shape of an oral cavity by at least one processor based on an image acquired from a three-dimensional scanner; displaying a screen comprising a first region on a display by the at least one processor, at least the three-dimensional image being displayed in the first region; receiving, by the at least one processor, a user input for selectively recording a predetermined region of the screen; and generating, by the at least one processor, a video image by recording a region of the screen corresponding to the user input in response to the user input, wherein the recorded region comprises a portion of the first region.

As one aspect of the present disclosure, a non-transitory computer-readable recording medium recording commands for processing a scan image of a three-dimensional scanner may be suggested. A non-transitory computer-readable recording medium according to the present disclosure, when executed by at least one processor, causes the at least one processor to perform an operation, wherein the commands cause the at least one processor to: generate a three-dimensional image of a shape of an oral cavity based on an image acquired from a three-dimensional scanner; display, on a display, a screen comprising a first region in which at least the three-dimensional image is displayed; receive a user input for selectively recording a predetermined region of the screen; and generate a video image by recording a region of the screen corresponding to the user input in response to the user input, and wherein the recorded region comprises a portion of the first region.

As one aspect of the present disclosure, a system for a three-dimensional scanning may be suggested. A system according to the present disclosure comprises a three-dimensional scanner comprising an input device and configured to scan a shape of an oral cavity; and an electronic device communicably coupled to the three-dimensional scanner, wherein the electronic device comprises: a communication circuit communicatively connected to the three-dimensional scanner; an input device; a display; and at least one processor, wherein the at least one processor is configured to: generate a three-dimensional image of the shape of the oral cavity based on an image acquired from the three-dimensional scanner via the communication circuit; display, on the display, a screen comprising a first region in which at least the three-dimensional image is displayed; receive a user input for selectively recording a predetermined region of the screen; and generate a video image by recording a region of the screen corresponding to the user input in response to the user input, and wherein the recorded region comprises a portion of the first region.

The method and the device for processing a scanned image, according to the present disclosure, may reduce the burden on a processor of an electronic device to enable effective scanning and recording operations, and may also reduce the size of a recording file to enable convenient delivery of the recording file to a dental laboratory or a manufacturer of a three-dimensional scanner, thereby increasing user convenience.

DETAILED DESCRIPTION

Figure 1:
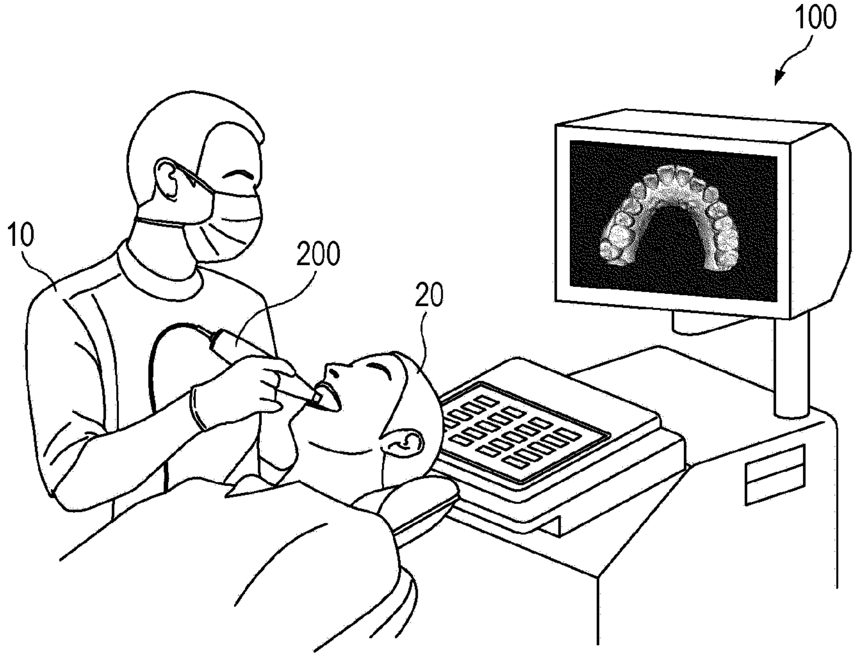
FIG. 1 illustrates acquiring an image of a patient's oral cavity by using an oral scanner according to various embodiments of the present disclosure.

Embodiments of the present disclosure are illustrated for describing the technical idea of the present disclosure. The scope of the claims according to the present disclosure is not limited to the embodiments described below or to the detailed descriptions of these embodiments.

All technical or scientific terms used in the present disclosure have meanings that are generally understood by a person having ordinary knowledge in the art to which the present disclosure pertains, unless otherwise specified. The terms used in the present disclosure are selected for the purpose of clearer explanation of the present disclosure, and are not intended to limit the scope of claims according to the present disclosure.

The expressions "include," "provided with," "have" and the like used in the present disclosure should be understood as open-ended terms connoting the possibility of inclusion of other embodiments, unless otherwise mentioned in a phrase or sentence including the expressions.

A singular expression used in the present disclosure can include meanings of plurality, unless otherwise mentioned, and the same is applied to a singular expression stated in the claims. The terms "first," "second," etc. used the present disclosure are used to distinguish a plurality of elements from one another, and are not intended to limit the order or importance of the relevant elements.

The term "unit" used in the present disclosure means a software element or hardware element, such as a field-programmable gate array (FPGA) or an application specific integrated circuit (ASIC). However, a "unit" is not limited to software and hardware. A "unit" may be configured to be stored in an addressable storage medium or may be configured to run on one or more processors. Therefore, for example, a "unit" may include elements, such as software elements, object-oriented software elements, class elements, and task elements, as well as processors, functions, attributes, procedures, subroutines, segments of program codes, drivers, firmware, micro-codes, circuits, data, databases, data structures, tables, arrays, and variables. Functions provided in elements and "unit" may be combined into a smaller number of elements and "units" or further subdivided into additional elements and "units."

The expression "based on" used in the present disclosure is used to describe one or more factors that influences a decision, an action of determination, or an operation described in a phrase or sentence including the relevant expression, and this expression does not exclude an additional factor influencing the decision, the action of determination, or the operation.

In the present disclosure, when a certain element is described as being "coupled to" or "connected to" another element, it should be understood that the certain element may be connected or coupled directly to the other element or that the certain element may be connected or coupled to the other element via a new intervening element.

In the present disclosure, artificial intelligence (AI) may refer to a technology that imitates human learning ability, reasoning ability, and perception ability and implements the same with a computer, and may include concepts of machine learning and symbolic logic. Machine learning (ML) may be an algorithmic technique that automatically classifies or learns the characteristics of input data. Artificial intelligence technology may use machine learning algorithms to analyze input data, learn the results of the analysis, and make determinations or predictions based on the results of the learning. Further, technologies that mimic the cognitive and decision-making functions of the human brain by using machine learning algorithms may also be considered to fall within the realm of artificial intelligence. For example, technical fields of language understanding, visual comprehension, reasoning and prediction, knowledge representation, and action control may be included.

In the present disclosure, machine learning may refer to a process of training a neural network model by using experience in processing data. Machine learning may imply that computer software improves its ability to process data on its own. A neural network model is constructed by modeling correlations between data, wherein the correlations may be represented by multiple parameters. The neural network model extracts features from given data and analyzes the features to derive correlations between data, and repeating this process to optimize the parameters of the neural network model may be referred to as machine learning. For example, a neural network model can learn the mapping (correlation) between inputs and outputs with respect to data provided as input-output pairs. Alternatively, even when only input data is provided, a neural network model can learn the relationships between the provided data by deriving regularities in the data.

In the present disclosure, an artificial intelligence learning model, a machine learning model, or a neural network model may be designed to implement a human brain structure on a computer and may include multiple network nodes that mimic neurons in a human neural network and have weights. Multiple network nodes may have connections to one another by mimicking the synaptic activity of neurons sending and receiving signals through synapses. In an artificial intelligence learning model, multiple network nodes can be located on layers having different depths to send and receive data based on convolutional connections. The artificial intelligence learning model may be, for example, an artificial neural network, a convolutional neural network, etc.

Hereinafter, embodiments of the present disclosure will be described with reference to the accompanying drawings. In the accompanying drawings, identical or corresponding elements are indicated by identical reference numerals. In the following description of embodiments, repeated descriptions of the identical or corresponding elements will be omitted. However, even when a description of an element is omitted, such an element is not intended to be excluded in an embodiment.

FIG. 1 illustrates acquiring an image of a patient's oral cavity by using an oral scanner 200 according to various embodiments of the present disclosure. According to various embodiments, the oral scanner 200 may be a dental medical device for acquiring an image of an oral cavity of a subject 20. As illustrated in FIG. 1, a user 10 (e.g., a dentist or a dental hygienist) may use the oral scanner 200 to acquire an image of the oral cavity of a subject 20 (e.g., a patient) from the subject 20. In another example, the user 10 may acquire an image of the oral cavity of the subject 20 from a diagnostic model (e.g., a plaster model or an impression model) that is made in the shape of the oral cavity of the subject 20. Hereinafter, for ease of explanation, the acquisition of an image of the oral cavity of the subject 20 will be described. However, the present disclosure is not limited thereto, and it is also possible to acquire an image of another part of the subject 20 (e.g., an ear of the subject 20). The oral scanner 200 may be shaped to be inserted into or removed from the oral cavity, and may be a handheld scanner for which a scanning distance and a scanning angle can be freely adjusted by the user 10.

The oral scanner 200 according to various embodiments may be inserted into the oral cavity and scan the interior of the oral cavity in a non-contact manner, thereby acquiring an image of the oral cavity. The image of the oral cavity may include at least one tooth, gingiva, and artificial structures insertable into the oral cavity (e.g., orthodontic devices including brackets and wires, implants, dentures, and orthodontic aids inserted into the oral cavity). The oral scanner 200 may use a light source (or a projector) to emit light to the oral cavity of the subject 20 (e.g., at least one tooth or gingiva of the subject 20), and may receive light reflected from the oral cavity of the subject 20 through a camera (or at least one image sensor). According to another embodiment, the oral scanner 200 may scan a diagnostic model of the oral cavity to acquire an image of the diagnostic model of the oral cavity. When the diagnostic model of the oral cavity is a diagnostic model that mimics the shape of the oral cavity of subject 20, an image of the diagnostic model of the oral cavity may be an image of the oral cavity of the subject. For ease of explanation, the following description assumes, but is not limited to, acquiring an image of the oral cavity by scanning the inside of the oral cavity of the subject 20.

The oral scanner 200 according to various embodiments may acquire a surface image of the oral cavity of the subject 20 as a two-dimensional image based on information received through a camera. The surface image of the oral cavity of the subject 20 may include at least one among at least one tooth, gingiva, artificial structure, cheek, tongue, or lip of the subject 20. The surface image of the oral cavity of subject 20 may be a two-dimensional image.

The two-dimensional image of the oral cavity acquired by the oral scanner 200 according to various embodiments may be transmitted to an electronic device 100 which is connected via a wired or wireless communication network. The electronic device 100 may be a computer device or a portable communication device. The electronic device 100 may generate a three-dimensional image (or, three-dimensional oral cavity image or a three-dimensional oral model) of the oral cavity, which is a three-dimensional representation of the oral cavity, based on the two-dimensional images of the oral cavity received from the oral scanner 200. The electronic device 100 may generate the three-dimensional image of the oral cavity by modeling the inner structure of the oral cavity in three dimensions, based on the received two-dimensional images of the oral cavity.

The oral scanner 200 according to another embodiment may scan the oral cavity of the subject 20 to acquire two-dimensional images of the oral cavity, generate a three-dimensional image of the oral cavity based on the acquired two-dimensional images of the oral cavity, and transmit the generated three-dimensional image of the oral cavity to the electronic device 100.

The electronic device 100 according to various embodiments may be communicatively connected to a cloud server (not shown). In this case, the electronic device 100 may transmit two-dimensional images of the oral cavity of the subject 20 or a three-dimensional image of the oral cavity to the cloud server, and the cloud server may store the two-dimensional images of the oral cavity of the subject 20 or the three-dimensional image of the oral cavity, which has been received from the electronic device 100.

According to another embodiment, in addition to a handheld scanner that is inserted into the oral cavity of subject 20, a table scanner (not shown) which is fixed and used in a specific location may be used as the oral scanner. The table scanner can generate a three-dimensional image of a diagnostic model of the oral cavity by scanning the diagnostic model of the oral cavity. In the above case, a light source (or a projector) and a camera of the table scanner are fixed, allowing the user to scan the diagnostic model of the oral cavity while moving the diagnostic model of the oral cavity.

Figure 2A:
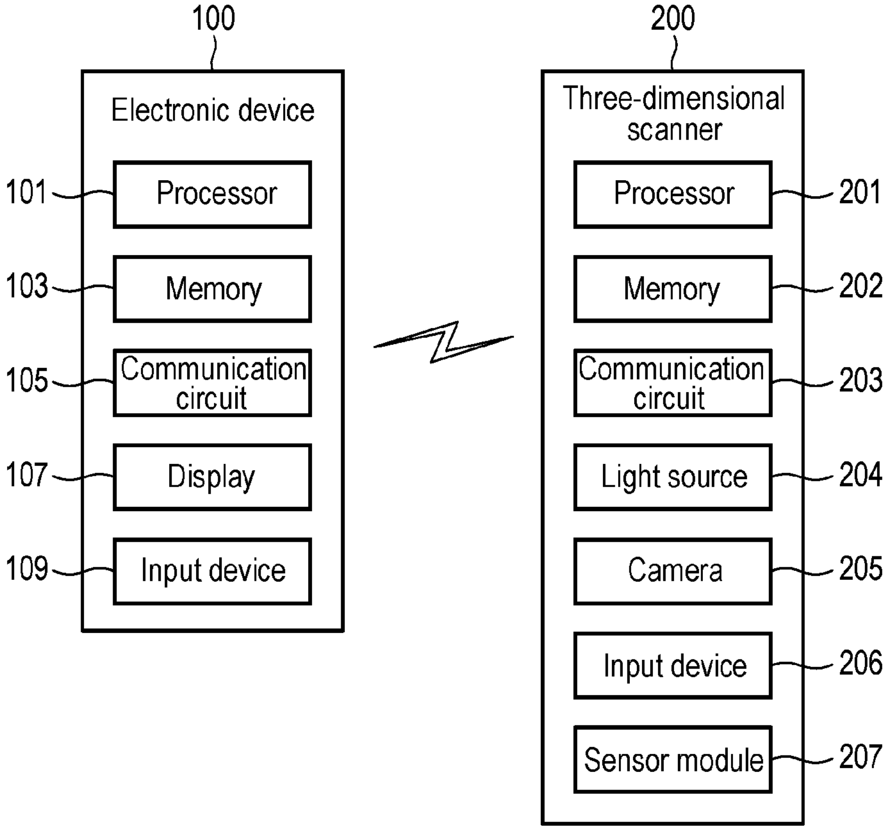
FIG. 2A is a block diagram of an electronic device and an oral scanner according to various embodiments of the present disclosure.

FIG. 2A is a block diagram of an electronic device 100 and an oral scanner 200 according to various embodiments of the present disclosure. The electronic device 100 and the oral scanner 200 may be communicatively connected to each other via a wired or wireless communication network, and may transmit and receive various types of data to and from each other.

The oral scanner 200 according to various embodiments may include a processor 201, a memory 202, a communication circuit 203, a light source 204, a camera 205, an input device 206, and/or a sensor module 207. At least one of the elements included in the oral scanner 200 may be omitted, or other elements may be added to the oral scanner 200. Additionally or alternatively, some elements may be integrated, or implemented as a single or multiple entities. At least some elements in the oral scanner 200 may be connected to each other via a bus, a general purpose input/output (GPIO), a serial peripheral interface (SPI), or a mobile industry processor interface (MIPI) so as to transmit and/or receive data and/or signals.

The processor 201 of the oral scanner 200 according to various embodiments is an element capable of performing operations or data processing related to control and/or communication of the elements of the oral scanner 200, and may be operatively coupled to the elements of the oral scanner 200. The processor 201 may load commands or data received from other elements of the oral scanner 200 into the memory 202, may process the commands or data stored in the memory 202, and may store resulting data. According to various embodiments, the memory 202 of the oral scanner 200 may store instructions for the above-described operations of the processor 201.

According to various embodiments, the communication circuit 203 of the oral scanner 200 may establish a wired or wireless communication channel with an external device (e.g., the electronic device 100), and may transmit and receive various types of data to and from the external device. According to an embodiment, for wired communication with the external device, the communication circuit 203 may include at least one port to be connected to the external device with a wired cable. In the above case, the communication circuit 203 may communicate with the external device that is connected to a wire via the at least one port. According to an embodiment, the communication circuit 203 may be configured to include a cellular communication module so as to be connected to a cellular network (e.g., 3G, LTE, 5G, Wibro, or Wimax). According to various embodiments, the communication circuit 203 may include a short-range communication module to transmit and receive data to and from external devices by using short-range communication (e.g., Wi-Fi, Bluetooth, Bluetooth Low Energy (BLE), UWB), but the present disclosure is not limited thereto. According to an embodiment, the communication circuit 203 may include a contactless communication module for contactless communication. The contactless communication may include at least one contactless proximity communication technology, for example, near-field communication (NFC) communication, radio frequency identification (RFID) communication, or magnetic secure transmission (MST) communication.

According to various embodiments, the light source 204 of the oral scanner 200 may emit light toward the oral cavity of the subject 20. For example, the light emitted from the light source 204 may be structured light having a predetermined pattern (e.g., a stripe pattern in which differently colored straight lines are continuously shown). The pattern of the structured light may be generated, for example, using a pattern mask or a digital micro-mirror device (DMD), but the present disclosure is not limited thereto. The camera 205 of the oral scanner 200 according to various embodiments may acquire an image of the oral cavity of the subject 20 by receiving light reflected by the oral cavity of the subject 20. The camera 205 may include, for example, a left camera corresponding to the left field of view and a right camera corresponding to the right field of view in order to construct a three-dimensional image by using optical triangulation. The camera 205 may include at least one image sensor, such as a CCD sensor or a CMOS sensor.

The input device 206 of the oral scanner 200 according to various embodiments may receive a user input for controlling the oral scanner 200. The input device 206 may include buttons for receiving push manipulation from the user 10, a touch panel for detecting touch from the user 10, and a speech recognition device including a microphone. For example, the user 10 may use the input device 206 to control the start or stop of scanning.

The sensor module 207 of the three-dimensional scanner 200 according to various embodiments may detect an operational state of the three-dimensional scanner 200 or an external environmental state (e.g., a user's motion) and generate an electrical signal corresponding to the detected state. The sensor module 207 may include, for example, at least one of a gyro sensor, an accelerometer, a gesture sensor, a proximity sensor, or an infrared sensor. The user 10 may use the sensor module 207 to control the start or stop of scanning. For example, when the user 10 is moving while holding the three-dimensional scanner 200 in hand, the three-dimensional scanner 200 may be controlled to start a scanning operation of the processor 201 when an angular velocity measured by the sensor module 207 exceeds a predetermined threshold.

According to an embodiment, the oral scanner 200 may start scanning by receiving a user input for starting scanning through the input device 206 of the oral scanner 200 or an input device 109 of the electronic device 100, or in response to processing in a processor 201 of the oral scanner 200 or the processor 101 of the electronic device 100. When the user 10 scans the inside of the oral cavity of the subject 20 by using the oral scanner 200, the oral scanner 200 may generate a two-dimensional image of the oral cavity of the subject 20, and may transmit the two-dimensional image of the oral cavity of the subject 20 to the electronic device 100 in real time. The electronic device 100 may display the received two-dimensional image of the oral cavity of the subject 20 on a display. Further, the electronic device 100 may generate (construct) a three-dimensional image of the oral cavity of the subject 20, based on the two-dimensional images of the oral cavity of the subject 20, and may display the three-dimensional image of the oral cavity on the display. The electronic device 100 may display the three-dimensional image, which is being generated, on the display in real time.

The electronic device 100 according to various embodiments may include at least one processor 101, at least one memory 103, a communication circuit 105, a display 107, and/or an input device 109. At least one of the elements included in the electronic device 100 may be omitted, or other elements may be added to the electronic device 100. Additionally or alternatively, some elements may be integrated, or implemented as a single or multiple entities. At least some elements in the electronic device 100 may be connected to each other via a bus, a general purpose input/output (GPIO), a serial peripheral interface (SPI), or a mobile industry processor interface (MIPI) so as to exchange data and/or signals.

According to various embodiments, the at least one processor 101 of the electronic device 100 may be an element capable of performing operations or data processing related to control and/or communication of the elements of the electronic device 100 (e.g., memory 103). The at least one processor 101 may be operatively coupled to the elements of the electronic device 100, for example. The at least one processor 101 may load commands or data received from other elements of the electronic device 100 into the at least one memory 103, may process the commands or data stored in the at least one memory 103, and store the resulting data.

According to various embodiments, the at least one memory 103 of the electronic device 100 may store instructions for operations of the at least one processor 101. The at least one memory 103 may store correlation models constructed based on a machine learning algorithm. The at least one memory 103 may store data (e.g., a two-dimensional image of the oral cavity acquired through oral scanning) received from the oral scanner 200.

According to various embodiments, the communication circuit 105 of the electronic device 100 may establish a wired or wireless communication channel with an external device (e.g., the oral scanner 200 or the cloud server), and may transmit or receive various types of data to or from the external device. According to an embodiment, for wired communication with the external device, the communication circuit 105 may include at least one port so as to be connected to the external device through a wired cable. In the above case, the communication circuit 105 may communicate with the external device that is connected to a wire via the at least one port. According to an embodiment, the communication circuit 105 may be configured to include a cellular communication module so as to be connected to a cellular network (e.g., 3G, LTE, 5G, Wibro, or Wimax). According to various embodiments, the communication circuit 105 may include a short-range communication module to transmit and receive data to and from external devices by using short-range communication (e.g., Wi-Fi, Bluetooth, Bluetooth Low Energy (BLE), or UWB), but the present disclosure is not limited thereto. According to an embodiment, the communication circuit 105 may include a contactless communication module for contactless communication. The contactless communication may include at least one contactless proximity communication technology, for example, near-field communication (NFC) communication, radio frequency identification (RFID) communication, or magnetic secure transmission (MST) communication.

The display 107 of the electronic device 100 according to various embodiments may display various screens based on control of the processor 101. The processor 101 may display, on the display 107, a two-dimensional image of the oral cavity of subject 20 received from the oral scanner 200 and/or a three-dimensional image of the oral cavity in which the inner structure of the oral cavity is modeled. For example, the two-dimensional image and/or the three-dimensional image of the oral cavity may be displayed through a particular application. In the above case, the user 10 may edit, save, and delete the two-dimensional image and/or the three-dimensional image of the oral cavity.

The input device 109 of the electronic device 100 according to various embodiments may receive commands or data, which are to be used by an element (e.g., the at least one processor 101) of the electronic device 100, from an external source (e.g., a user) of the electronic device 100. The input device 109 may include, for example, a microphone, a mouse, or a keyboard. According to an embodiment, the input device 109 may be implemented in the form of a touch sensor panel that may be coupled to the display 107 to recognize contact or proximity of various external objects.

Figure 2B:
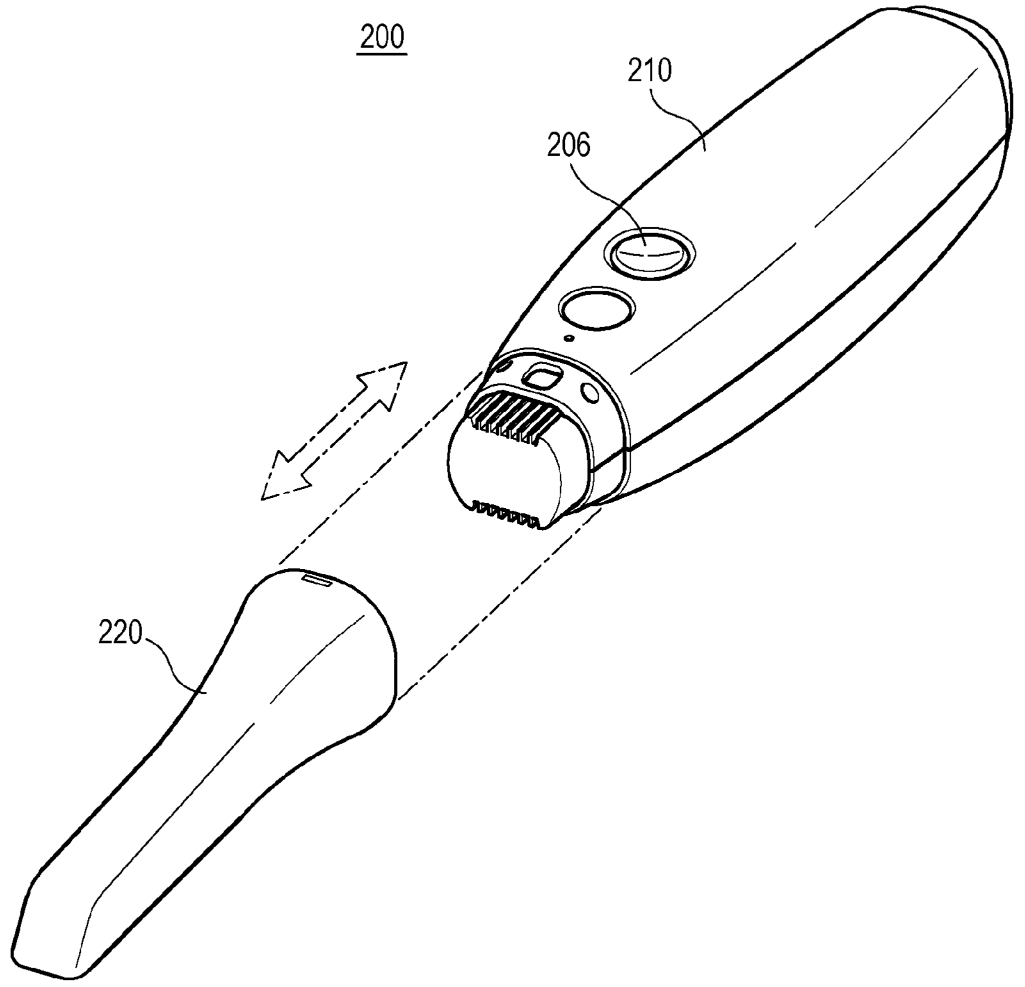
FIG. 2B is a perspective view of an oral scanner according to various embodiments of the present disclosure.

FIG. 2B is a perspective view of an oral scanner 200 according to various embodiments. The oral scanner 200 according to various embodiments may include a body 210 and a probe tip 220. The body 210 of the oral scanner 200 may be formed in a shape that is easy for the user 10 to grip and use by hand. Also, the probe tip 220 may be shaped for easy insertion into and removed from the oral cavity of the subject 20. Further, the body 210 may be coupled to and detachable from the probe tip 220. Inside the body 210, the elements of the oral scanner 200 illustrated in FIG. 2A may be disposed. An opening may be formed at one end of the body 210 so that light output from the light source 204 can be emitted onto the subject 20 through the opening. Light emitted through the opening may be reflected by the subject 20 and introduced again through the opening. The reflected light introduced through the opening may be captured by the camera to generate an image of the subject 20. The user 10 may start scanning by using the input device 206 (e.g., a button) of the oral scanner 200. For example, when the user 10 touches or presses the input device 206, light from the light source 204 may be emitted onto the subject 20.

Figure 3:
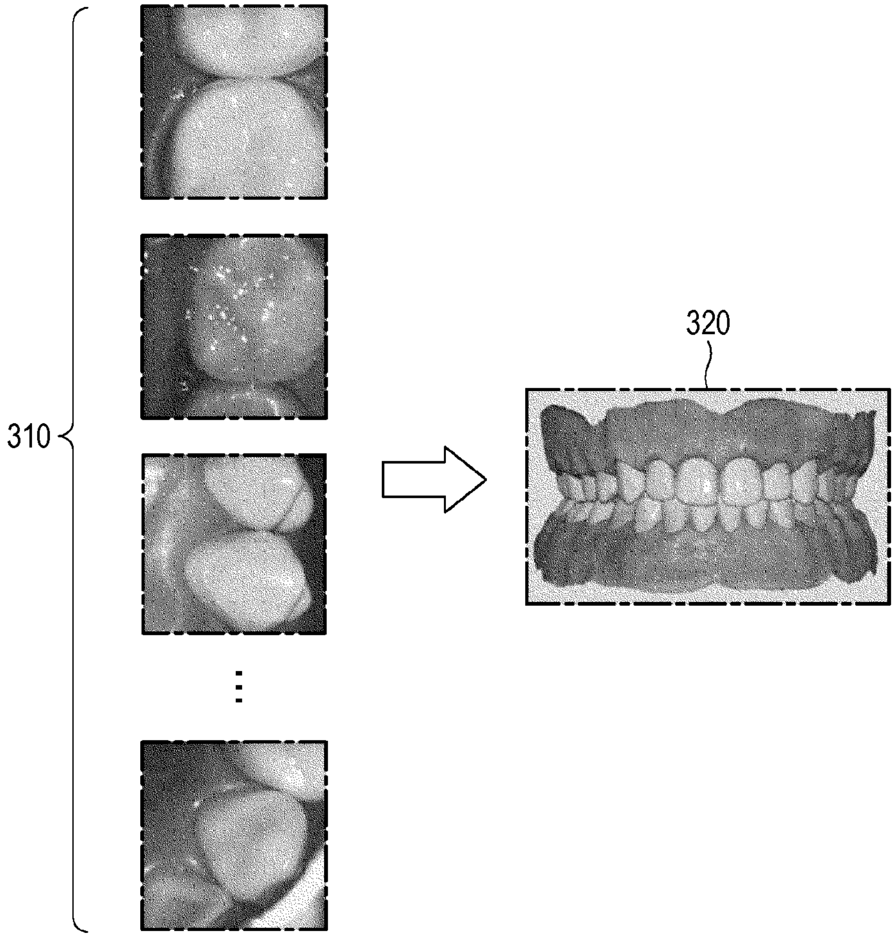
FIG. 3 illustrates a method for generating a three-dimensional image of an oral cavity according to various embodiments of the present disclosure.

FIG. 3 illustrates a method for generating a three-dimensional image 320 of an oral cavity according to various embodiments. The user 10 may move the oral scanner 200 to scan the inside of the oral cavity of the subject 20, in which case the oral scanner 200 may acquire multiple two-dimensional images 310 of the oral cavity of the subject 20. For example, the oral scanner 200 may acquire a two-dimensional image of a region including a front tooth of the subject 20, a two-dimensional image of a region including a molar of the subject 20, and the like. The oral scanner 200 may transmit the multiple acquired two-dimensional images 310 to the electronic device 100.

According to various embodiments, the electronic device 100 may convert each of the multiple two-dimensional images 310 of the oral cavity of the subject 20 into a set of multiple points having three-dimensional coordinate values. For example, the electronic device 100 may convert each of the multiple two-dimensional images 310 into a point cloud, which is a set of data points having three-dimensional coordinate values. For example, a set of point clouds, which are three-dimensional coordinate values based on the multiple two-dimensional images 310, may be stored as raw data for the oral cavity of subject 20. By aligning the point clouds, each of which is a set of data points having three-dimensional coordinate values, the electronic device 100 may complete a full dental model.

According to various embodiments, the electronic device 100 may reconfigure (reconstruct) a three-dimensional image of the oral cavity. For example, the electronic device 100 may reconfigure the three-dimensional image 320 of the oral cavity of the subject 20 by merging a set of point clouds stored as raw data by using a Poisson algorithm to reconfigure multiple points and transforming the points into a closed three-dimensional surface.

Figure 4:
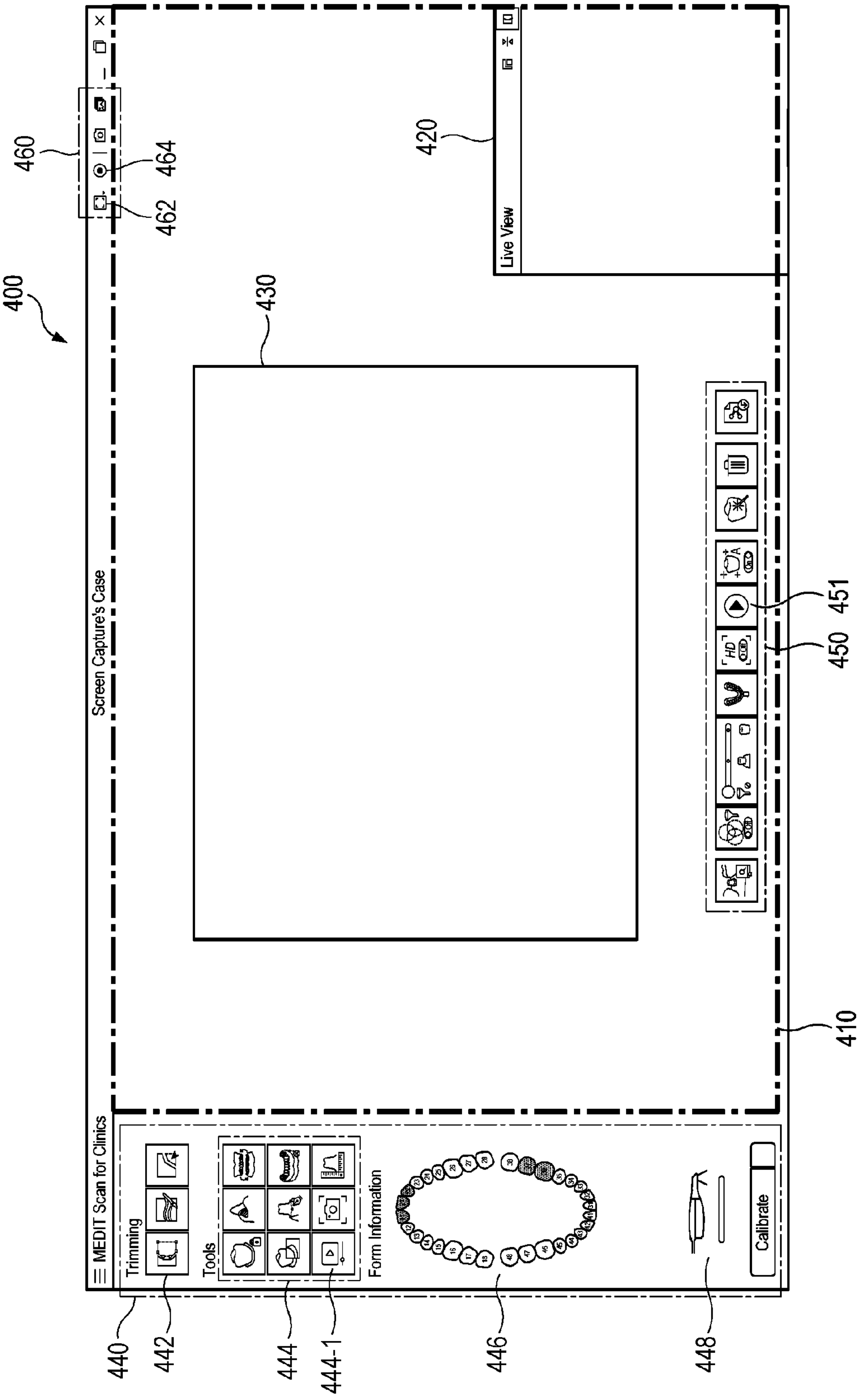
FIG. 4 illustrates a data acquisition program screen displayed on a display of an electronic device according to various embodiments of the present disclosure.

FIG. 4 illustrates a data acquisition program screen 400 displayed on the display 107 of the electronic device 100 according to various embodiments of the present disclosure. The electronic device 100 may execute a data acquisition program by the processor 101. The data acquisition program may be stored in the memory 103 as an application. When the data acquisition program is executed by the processor 101, the electronic device 100 may display, on the display 107, the two-dimensional images 310 received from the oral scanner 200 and the three-dimensional image generated based thereon.

When the data acquisition program is executed, the electronic device 100 may display images scanned by the oral scanner 100 and may provide user interfaces for processing and manipulating the images. In an embodiment, the data acquisition program screen 400 includes user interfaces including a data display region 410, a live view region 420, a model view region 430, a function box region 440, a function option region 450, and an icon display region 460. The user interfaces are illustrative, and the data acquisition program screen 400 may include any additional user interfaces as necessary.

The data display region 410 is a region for displaying images received from the oral scanner and a three-dimensional image generated based thereon. In an embodiment, the data display region 410 includes the live view region 420 and the model view region 430. In an embodiment, the data display region 410 includes the function option region 450.

The live view region 420 displays images received from the oral scanner 100. In an embodiment, the electronic device 100 may display two-dimensional images of the oral cavity, which is currently being scanned by the oral scanner 200, on the live view region 420 in real time. The live view region 420 is moveable and resizable by the user and is separable from the data acquisition program screen 400. In an embodiment, the user can configure the live view region 420 so as not to be displayed.

The electronic device 100 may display, in the model view region 430, a three-dimensional image model generated from the two-dimensional images acquired from the oral scanner 100.

The function box region 440 includes a user interface for providing functions of modifying/editing or analyzing the displayed three-dimensional image model, and a user interface for displaying a device state. In an embodiment, the function box region 440 includes a trimming function interface 442 for selecting and deleting unnecessary portions of data acquired during a scanning process, a function tool interface 444 for editing or storing a generated three-dimensional image, a treatment information interface 446 for displaying an image regarding treatment information of each tooth, and a device state display interface 448 for displaying the device state of the oral scanner 200. For example, the functional tool interface 444 includes a playback control interface 444-1 for playing back a recorded screen to be described later in relation to FIGS. 6A to 6E and FIG. 7.

In response to a user input of selecting one function interface in the function box regions 440, the electronic device 100 may display detailed options thereof in the function option region 450. In an embodiment, when the user selects the playback control interface 444-1 of the function tool interface 444 in the function box region 440, the electronic device 100 may display, in the function option region 450, options for playback of the recorded screen, such as a play/stop button, an interface for controlling a playback position/speed, etc. When a function that does not require detailed options is selected in the function box region 440, the function option region 450 may not be displayed.

The icon display region 460 is a region for providing screen recording and capturing functions, and may include a recording region configuration icon 462 and a recording start/end icon 464. The recording region configuration icon 462 provides an interface for configuring a screen region to be recorded, which will be described later in connection with FIG. 8. The recording start/end icon 464 provides an interface for starting or ending recording of the data acquisition program screen 400, which will be described later in connection with FIGS. 6A through 6E and FIG. 7.

Figure 5:
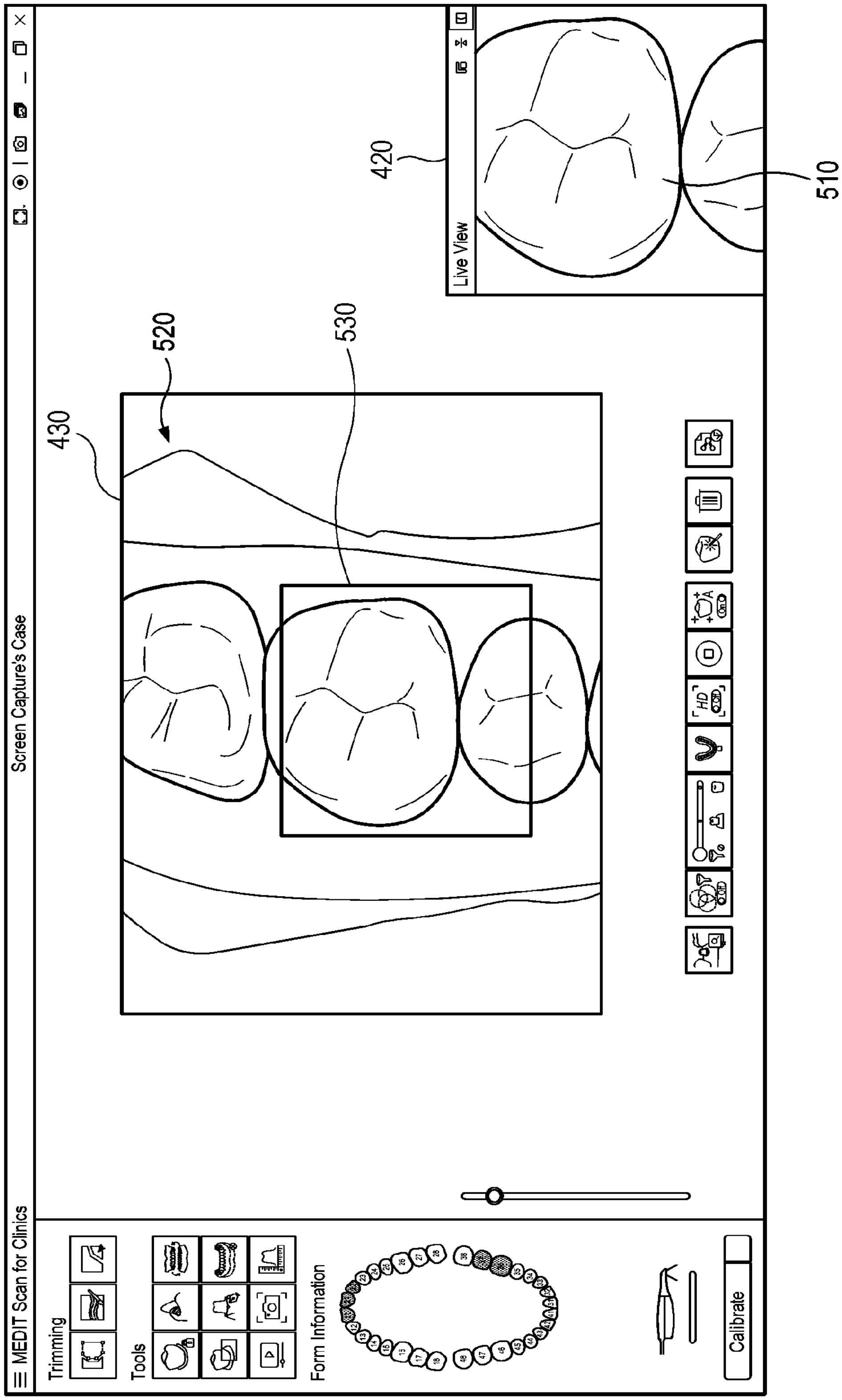
FIG. 5 illustrates a data display region of a data acquisition program screen during oral scanning according to various embodiments of the present disclosure.

FIG. 5 illustrates the data display region 410 of the data acquisition program screen 400 during oral scanning according to various embodiments of the present disclosure. The electronic device 100 may display an oral cavity image 510 received from the oral scanner 200 in the live view region 420 of the data acquisition program 400. The oral cavity image 510 displayed in the live view region 420 may be a two-dimensional image.

The electronic device 100 may convert multiple images received from the oral scanner 200 into a three-dimensional image 520, for example, by using the method described with respect to FIG. 3. The three-dimensional image 520 acquired by the conversion may be displayed in the model view region 430. A region 530 corresponding to the oral cavity image 510 displayed in the live view region 420 may be displayed in the form of a rectangle in the model view region 430.

In an embodiment, the size of the generated three-dimensional image 520 may change as various regions of the oral cavity are scanned at various angles. In an embodiment, the model view region 430 may be enlarged/reduced based on the size of the generated three-dimensional image 520.

The process of change in the three-dimensional image 520 that is generated as scanning progresses may be recorded by recording at least a partial region of the data acquisition program screen 400. In an embodiment, the electronic device 100 may start or end screen recording in response to a user input of selecting the recording start/end icon 464 in the icon display region 460 of the data acquisition program screen 400.

In an embodiment, when a user clicks (initiates input) the input device 206 of the oral scanner 200 or a capture/recording button (not shown), the electronic device 100 may start or end screen recording in response thereto. Additionally or alternatively, the screen recording may be started/ended in response to a user input, such as a double-click or long-click on the input device 206 of the oral scanner 200. According to the embodiment, when it is necessary to start/end recording while operating the oral scanner 200, the user does not need to separately manipulate the input device 109 of the electronic device 100 coupled to the oral scanner 200, thereby increasing user convenience and also contributing to the hygiene of the user operating the oral scanner.

In an embodiment, the electronic device 100 may automatically start screen recording when a preconfigured condition is met. For example, during scanning of the oral cavity using the oral scanner 200, the electronic device 100 may detect that an image received from the oral scanner 200 or a generated three-dimensional image includes teeth. The electronic device 100 may automatically start screen recording in response to the detection of the teeth. In an embodiment, the electronic device 100 may determine whether the image received from the oral scanner 200 or the generated three-dimensional image includes teeth, by using a machine learning model which has been trained using images of teeth as training data. In the embodiment, the electronic device 100 may stop screen recording when the predetermined condition is met, such as when a tooth is not detected in the scanned image or three-dimensional image for a predetermined time. According to the embodiment, the user does not need to manipulate the input device 109 of the electronic device 100, which is coupled to the oral scanner 200, in order to start/end recording, thereby increasing user convenience and contributing to user hygiene. Also, since recording is not performed while the oral cavity is not being scanned, it is possible to prevent unnecessary portions from being recorded.

When the screen recording ends, the electronic device 100 may store the recording as a video image file in the memory 103 of the electronic device 100. In an embodiment, the video image file may be stored in a remote storage, such as a cloud server. In an embodiment, the electronic device 100 may adjust the resolution of the recorded video based on a user input.

According to embodiments of the present disclosure, the electronic device 100 may determine, based on a user input from the user of the oral scanner 200, a target region, which is to be recorded when recording the data acquisition program screen 400. In an embodiment, the user may directly or indirectly input, into the electronic device 100, a user input for selecting a desired recording region from among preconfigured recording regions. As described later in connection with the embodiment illustrated in FIG. 8, the electronic device 100 may select one of the entire region of the data acquisition program screen 400, the data display region 410 of the data acquisition program screen 400, and the model view region 430 of the data acquisition program screen 400 as a recording region in response to the user input. In an embodiment, the electronic device 100 may adjust, based on the user input, the location and size of the recording region.

Figure 6A:
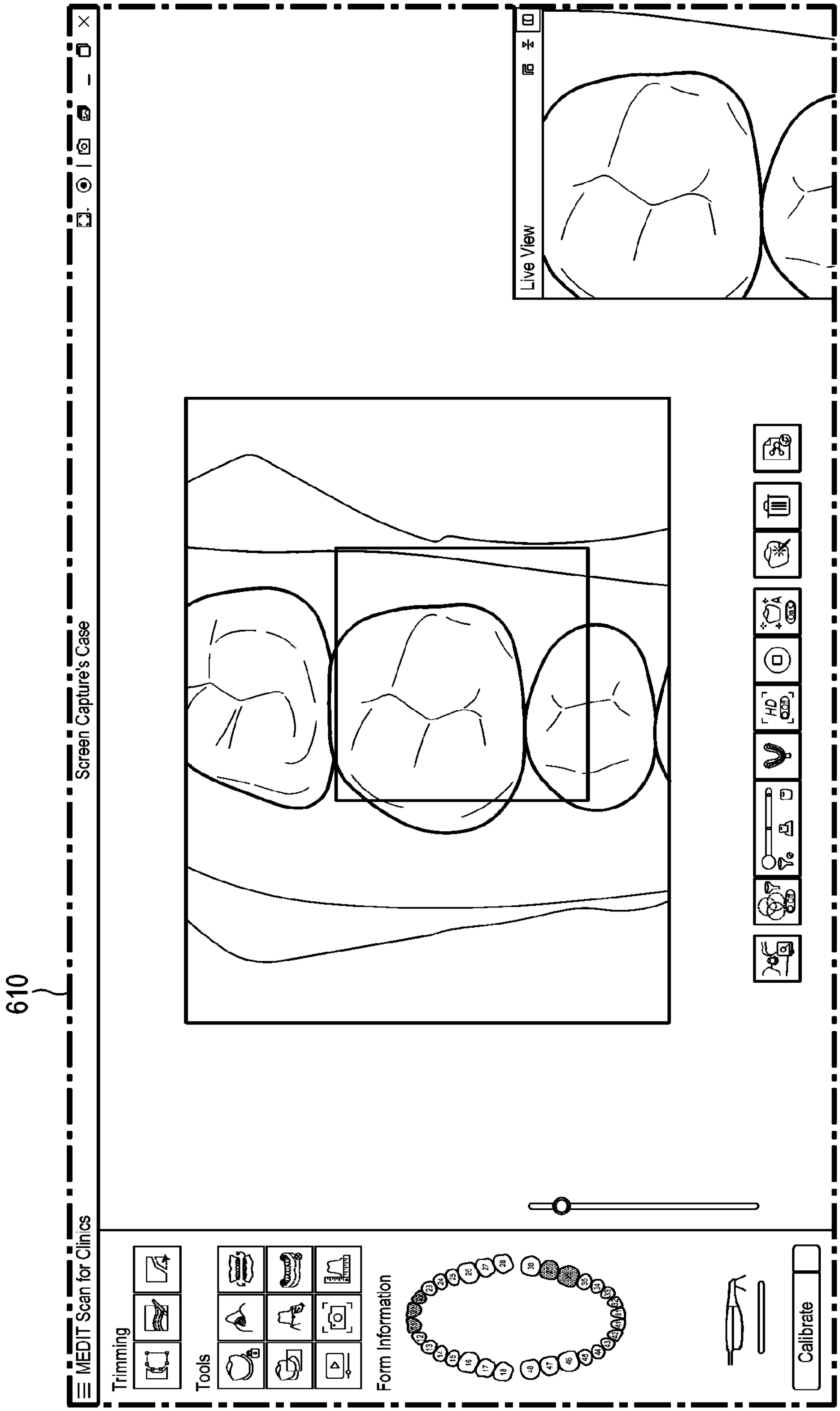
FIGS. 6A to 6E illustrate operations of recording a data acquisition program screen according to various embodiments of the present disclosure.

FIGS. 6A to 6E illustrate operations of recording the data acquisition program screen 400 according to various embodiments of the present disclosure. FIG. 6A illustrates an embodiment of recording the entire region of the data acquisition program screen 400. As illustrated in FIG. 6A, when screen recording starts, the electronic device 100, for example, displays a recording region with a dashed line 610 to allow a user to know that the screen recording is currently in progress and which region is currently being recorded. The recording region may be displayed using methods other than the dashed line 610, such as a dotted line or a solid line, and may be blinking or color-highlighted.

In an embodiment, the electronic device 100 may configure a recording region by using a screen coordinate system. According to the embodiment illustrated in FIG. 6A, the electronic device 100 sets the top-left region of the entire region of the data acquisition program screen 400 as the origin (0, 0). The electronic device 100 determines the coordinates of end points of the recording region based on the size (width and height) of the entire region of the data acquisition program screen 400 relative to the set origin. Then, the electronic device 100 converts the coordinates of the end points to the screen coordinates of the display, and determines the recording region based on the acquired coordinates.

Recording the entire region of the data acquisition program screen 400, as illustrated in FIG. 6A, has an advantage that information regarding user interfaces (e.g., the function box region 440, the function option region 450, and the icon display region 460) selected by the user, and information regarding changes in an image displayed in the live view region 420 and an image displayed in the model view region 430 during scanning are all recorded.

Figure 6B:
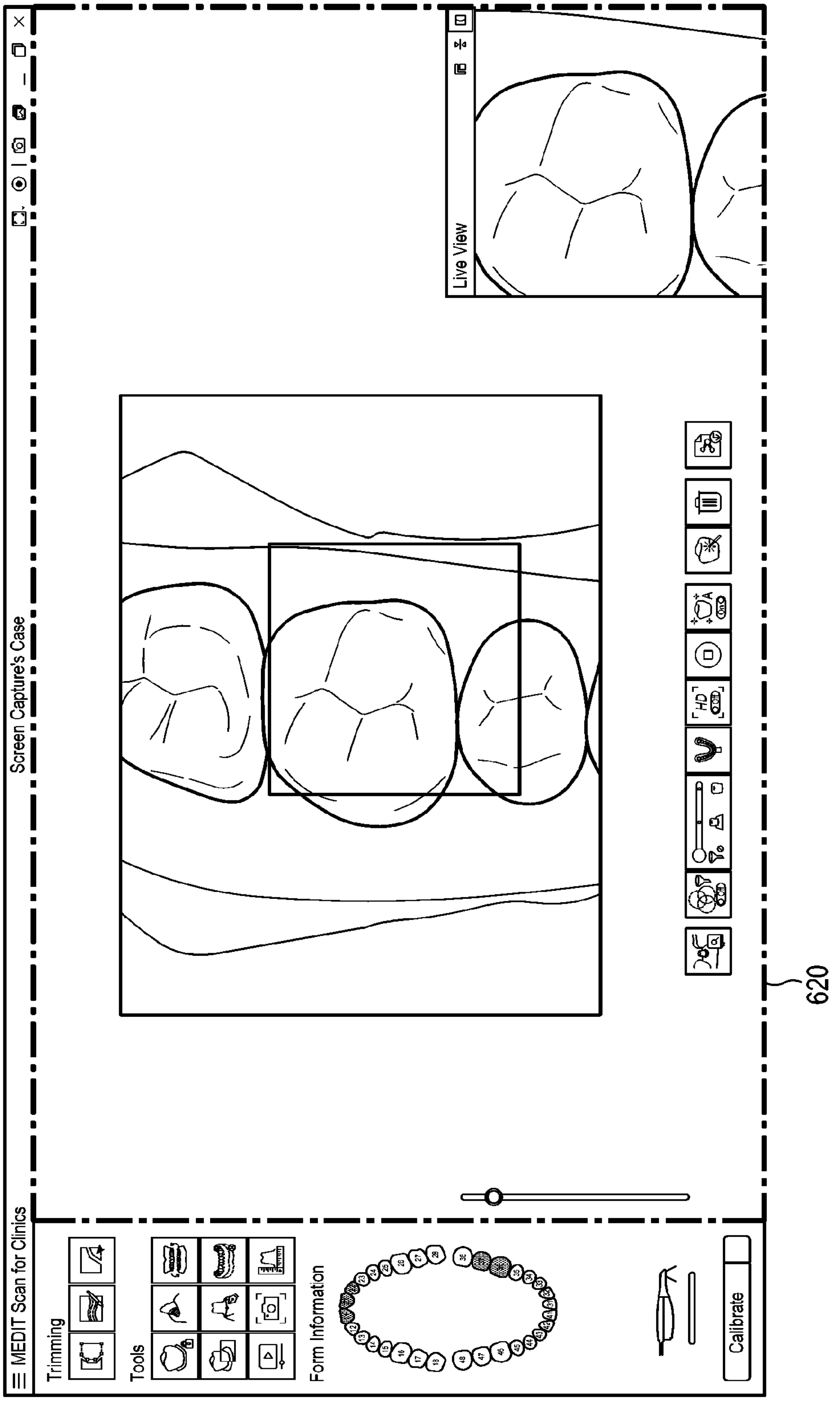

FIG. 6B illustrates an embodiment of recording the data display region 410 of the data acquisition program screen 400. As illustrated in FIG. 6B, when screen recording starts, the electronic device 100, for example, displays a recording region with a dashed line 620 to allow a user to know that the screen recording is currently in progress and which region is currently being recorded.

According to the embodiment illustrated in FIG. 6B, the electronic device 100 sets the top-left region of the data display region 410 of the data acquisition program screen 400 as the origin (0, 0). The electronic device 100 determines the coordinates of end points of the recording region based on the size (width and height) of the data display region 410 of the data acquisition program screen 400 relative to the set origin. Then, the electronic device 100 converts the coordinates of the end points to the screen coordinates of the display, and determines the recording region based on the acquired coordinates.

Recording only the data display region of the data acquisition program screen 400, as illustrated in FIG. 6B, has an advantage that information about user interfaces, such as the function box region 440 and the icon display region 460, selected by the user is not recorded, but information about changes in an image displayed in the live view region 420 and an image displayed in the model view region 430 during scanning is recorded. Further, since the embodiment illustrated in FIG. 6B has a relatively small recording region compared to the embodiment illustrated in FIG. 6A, the processor's burden for screen recording may be reduced, thereby offering an advantage of reducing adverse effects on a scanning operation. Furthermore, since the embodiment illustrated in FIG. 6B has a relatively small recording region compared to the embodiment illustrated in FIG. 6A, the size of a generated recording file may be reduced, thereby increasing user convenience in storing the recording file or delivering the recording file to a third party.

Figure 6C:
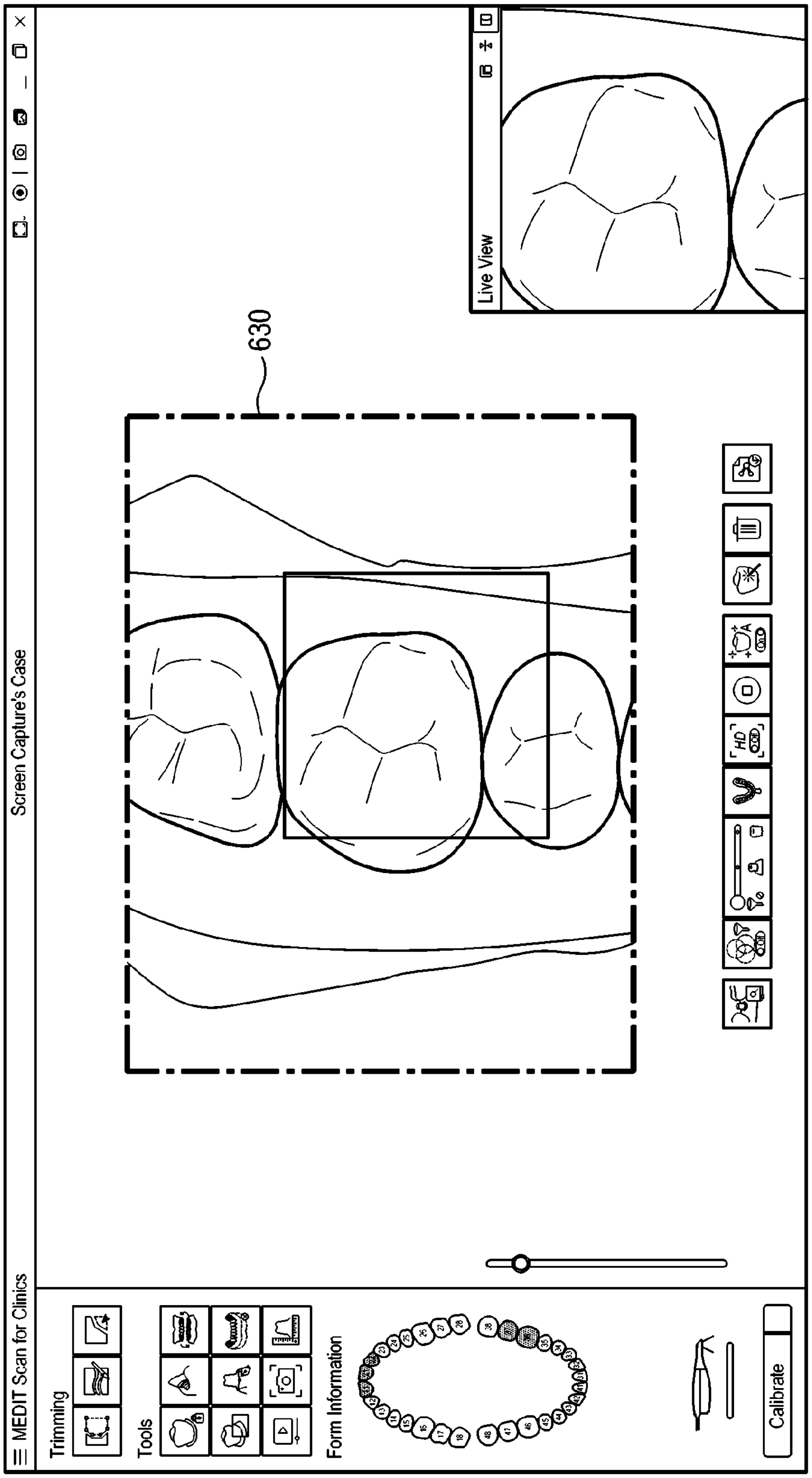

FIG. 6C illustrates an embodiment of recording only the model view region 430 of the data acquisition program screen 400. As illustrated in FIG. 6C, when screen recording starts, the electronic device 100, for example, displays a recording region with a dashed line 630 to allow a user to know that the screen recording is currently in progress and which region is currently being recorded.

According to the embodiment illustrated in FIG. 6C, the electronic device 100 sets the top-left region of the model view region 430 of the data acquisition program screen 400 as the origin (0, 0). The electronic device 100 determines the coordinates of end points of the recording region based on the size (width and height) of the model view region 430 of the data acquisition program screen 400 relative to the set origin. Then, the electronic device 100 converts the coordinates of the end points to the screen coordinates of the display, and determines the recording region based on the acquired coordinates.

When recording only the model view region of the data acquisition program screen 400 as illustrated in FIG. 6C, the function box region 440, the function option region 450, and the icon display region 460 are excluded from being recorded. In this regard, the embodiment illustrated in FIG. 6C has a relatively small recording region compared to the embodiments illustrated in FIGS. 6A and 6B, so the processor's burden for screen recording may be reduced, thereby offering an advantage of reducing adverse effects on a scanning operation. Further, since the embodiment illustrated in FIG. 6B has a relatively small recording region compared to the embodiments illustrated in FIGS. 6A and 6B, the size of a generated recording file may be reduced, thereby increasing user convenience in storing the recording file or delivering the recording file to a third party.

Figure 6D:
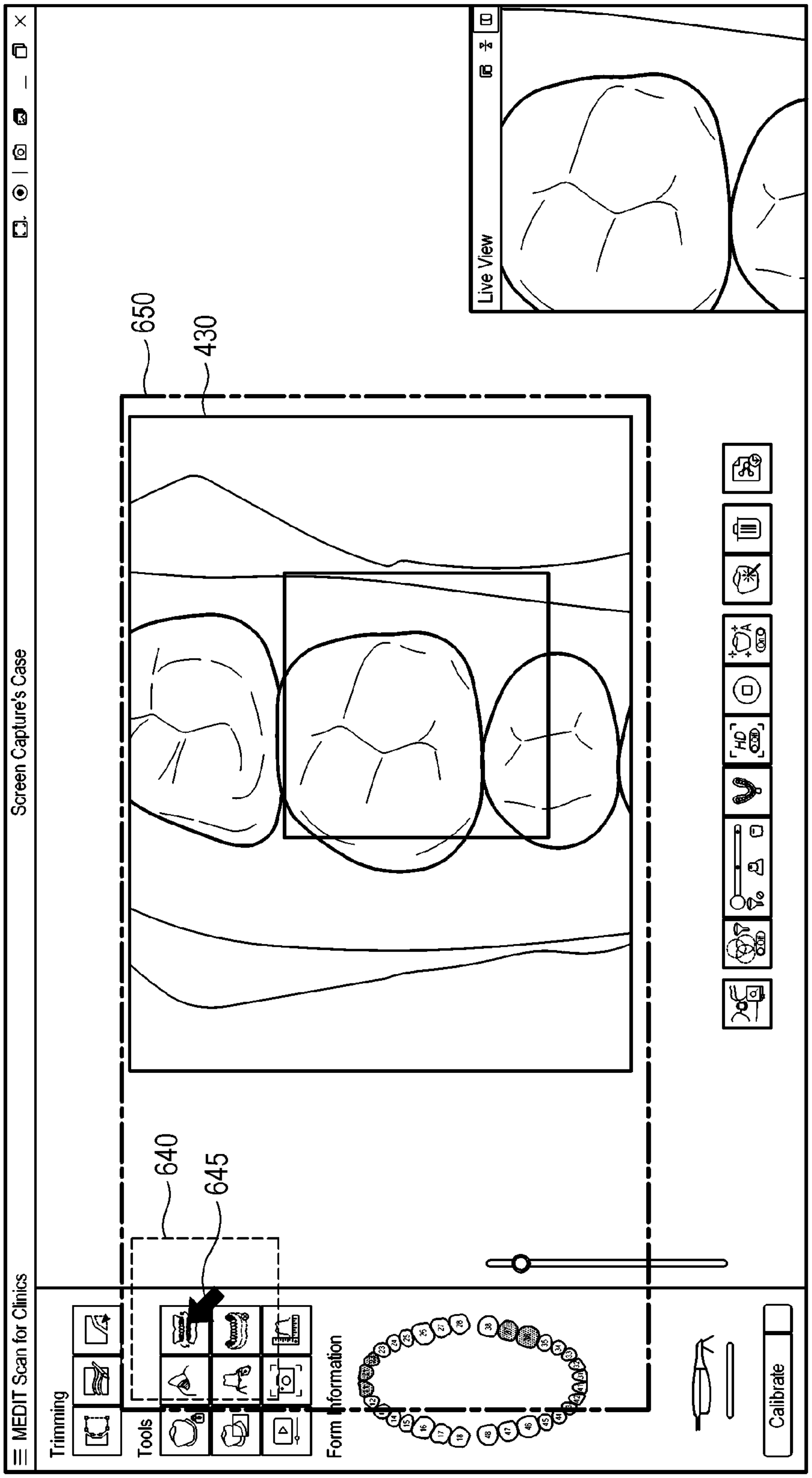

In an embodiment, the electronic device 100 tracks and records a region corresponding to a location of a user input, received via the input device 109 of the electronic device 100 or the input device 206 of the oral scanner 200, on the display. FIG. 6D illustrates an embodiment of tracking and recording a region corresponding to the location of the user input. In the embodiment of FIG. 6D, the region corresponding to the user input location is a region that includes a pointer 645 displayed on the display of the electronic device 100. The pointer 645 may be a mouse pointer displayed on the display 107, and the region corresponding to the user input location may be a region 640 that extends a predetermined distance upward, downward, leftward, and rightward from the pointer 645. In an embodiment, the data acquisition program may provide a user interface (not shown) for configuring the area of the region corresponding to the user input location.

As illustrated in FIG. 6D, the electronic device 100 displays, on the display 107, the pointer 645 that corresponds to the location of a user input received via the input device 109 of the electronic device 100 or the input device 206 of the oral scanner 200. When screen recording starts, the electronic device 100 may record a region corresponding to the location of the pointer 645.

In an embodiment, the electronic device 100 may record a region 650 that includes all of additional regions along with the region 640 corresponding to the user input location. In another embodiment, the electronic device 100 may record a region (not shown) that includes the entire region from the additional regions to the pointer 645 corresponding to the user input location. The additional regions may include the model view region 430. However, this is only an example, and any other regions may be recorded along with the region corresponding to the user input location. In an embodiment, the user-designated region that will be described later with reference to FIG. 7 may be recorded along with the region 640 corresponding to the user input location.

According to the embodiment illustrated in FIG. 6D, the electronic device 100 configures, as a recording region, a region that includes both a region corresponding to a user input location and additional regions to be included in the recording region, and then performs recording.

In the embodiment illustrated in FIG. 6D, the electronic device 100 configures the region 650, which includes the model view region 430 along with the region 640 corresponding to the user input location, as a recording region. The electronic device 100 configures, as the origin (0, 0), the top-left region of the minimum region that includes both the region 640 corresponding to the user input position and the model view region 430. Further, the electronic device 100 determines the bottom-right region of the minimum region that includes both the region 640 corresponding to the user input location and the model view region 430 as endpoint coordinates. Then, the electronic device 100 converts the coordinates of the end points into screen coordinates of the display, and determines the recording region based on the acquired coordinates.

As described with respect to FIGS. 6A to 6C, the electronic device 100, for example, may display the recording region with the dashed line 610 to allow the user to know that screen recording is currently in progress and which region is currently being recorded.

When the region 650 that includes both the region 640 corresponding to the location of the user input and the additional regions is recorded, the size of the entire recording region 650 may change as the location of the user input changes. In this case, the electronic device 100 may resize a recorded image to fit the size of a video image file in which the recorded image is stored.

Recording the region 650, which includes the region 640 corresponding to the user input location and any necessary additional regions as illustrated in FIG. 6D, has an advantage that the recording region may minimally include the process in which the user uses the functions of the data acquisition program.

Figure 6E:
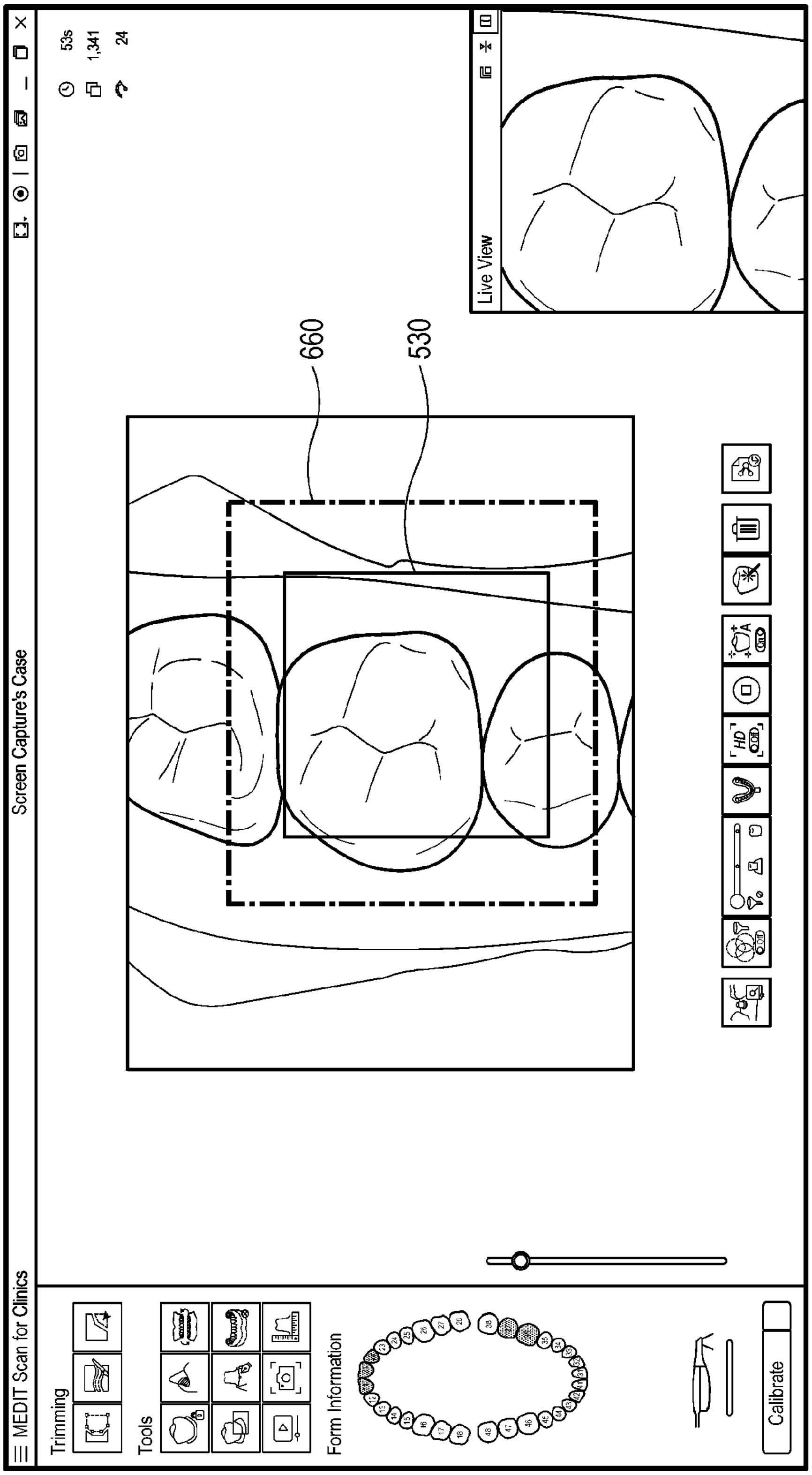

FIG. 6E illustrates an embodiment of recording a region that includes the scanning region 530 of the data acquisition program screen 400. Specifically, the electronic device 100 may record only the region 530 corresponding to an oral cavity image currently being scanned, or may record only a region 660 that extends beyond the region 530 by a predetermined range. The expanded region 660 may be a region 640 acquired by extending the region 530, which corresponds to the oral cavity image currently being scanned, by a predetermined distance upward, downward, leftward, and rightward. When the electronic device 100 is recording the region 640, the electronic device 100 may display, as illustrated in FIG. 6E, the recording region with a dashed line 660 to allow a user to know that screen recording is currently in progress, and the extent of the region being currently recorded.

As illustrated in FIG. 6E, recording only the region 530 corresponding to the oral cavity image currently being scanned on the data acquisition program screen 400, or the expanded region 660 including the same may allow for recording only the minimal region of interest generated as a three-dimensional image model, thereby increasing user convenience in storing a recording file or delivering the recording file to a third party.

Figure 7:
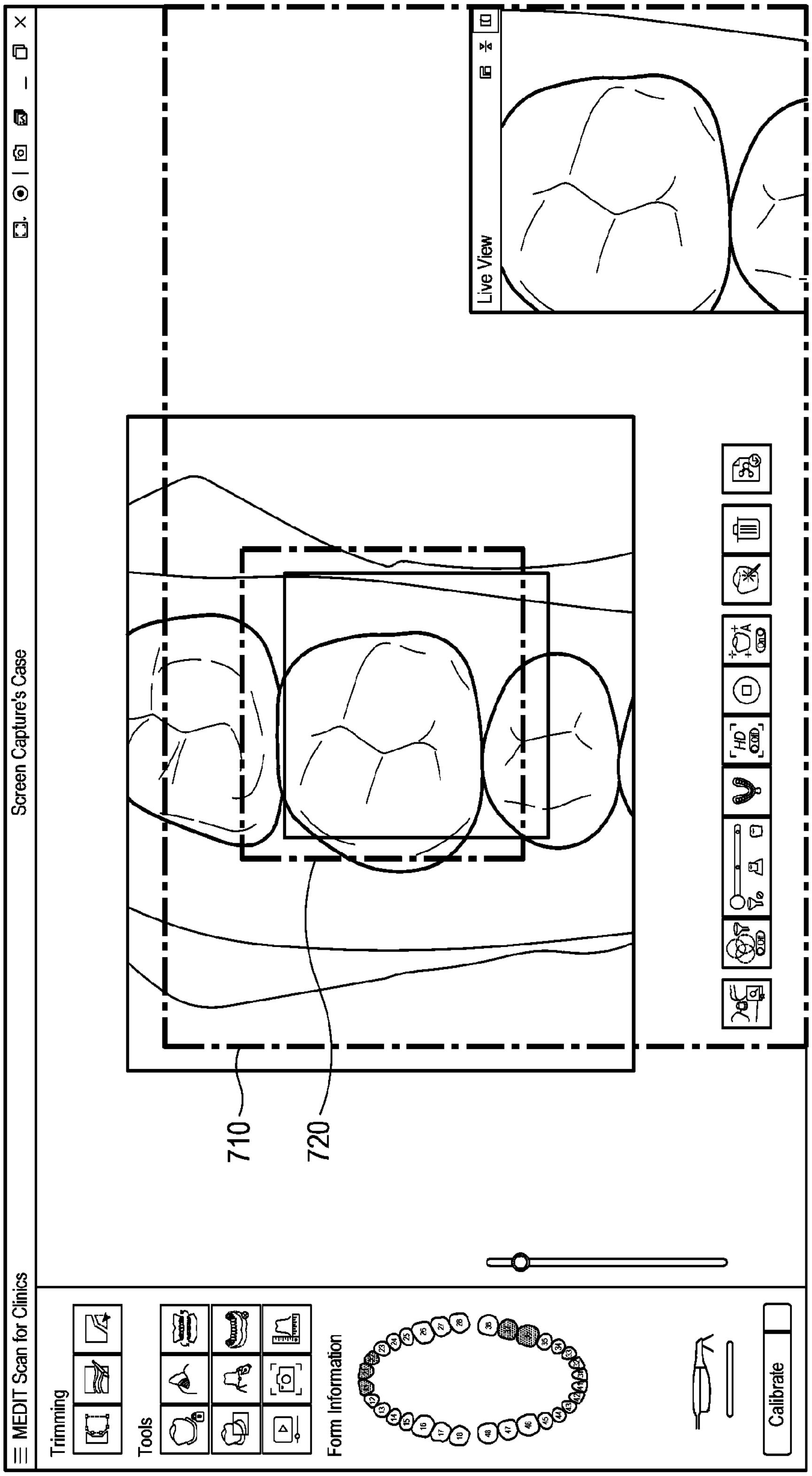
FIG. 7 illustrates a recording region configured in a data acquisition program screen according to various embodiments of the present disclosure.

In an embodiment, the electronic device 100 may selectively record only a portion of the region of the data acquisition program screen 400 based on a user input for arbitrarily configuring a region to be recorded. FIG. 7 illustrates a recording region configured on the data acquisition program screen 400 according to various embodiments of the present disclosure. In the embodiment illustrated in FIG. 7, the user-configured recording region is indicated by dashed lines 710 and 720.

In an embodiment, a user uses an input device (e.g., a mouse, a touch-sensitive display, etc.) of the electronic device 100 to configure a desired recording region. The user may configure the recording region through a drag input. The user may configure a necessary recording region in consideration of the information to be stored in a recording file. A recording region may be configured before or during scanning. In an embodiment, the user may configure a desired recording region through an input device of the oral scanner 200 and/or movement of the oral scanner 200. For example, a recording region may be configured based on the movement of the oral scanner detected through the sensor module 207 of the oral scanner 200. In an embodiment, the region 710 including the live view region 420 and the model view region 430 may be configured as a recording region. Alternatively, only a portion 720 of the model view region 430 may be configured as a recording region. Without being limited thereto, the recording region may be arbitrarily configured.

Figure 8:
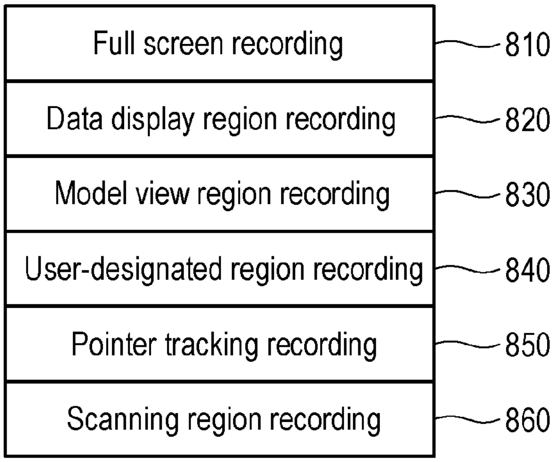
FIG. 8 illustrates a menu screen for determining a region to be recorded in a data acquisition program according to various embodiments of the present disclosure.

FIG. 8 illustrates a menu screen 800 for determining a region to be recorded on the data acquisition program screen 400 according to various embodiments of the present disclosure. In an embodiment, the menu screen in FIG. 8 may be displayed when the recording region configuration icon 462 in the icon display region 460 on the data acquisition program screen 400 is selected.

As illustrated in FIG. 8, a user of the oral scanner 200 and the data acquisition program screen 400 may select one from among full screen recording 810, data display region recording 820, model view region recording 830, user-designated region recording 840, pointer tracking recording 850, and scanning region recording 860. In an embodiment, based on a user input via the input device 206 or the sensor module 207 of the oral scanner 200, one recording region may be selected from among the full screen recording 810, the data display region recording 820, the model view region recording 830, the user-designated region recording 840, the pointer tracking recording 850, and the scanning region recording 860. For example, the electronic device 100 may sequentially change a recording region when receiving a user input such as a double-click or long-click on the input device 206 from the oral scanner 200. Additionally or alternatively, the electronic device 100 may sequentially change the recording region when receiving a signal, which indicates that the oral scanner 200 has been shaken or a predetermined gesture has been made, through the sensor module 207 of the oral scanner 200.

When the user selects the full screen recording 810, the entire region of the data acquisition program screen 400, for example, as illustrated in FIG. 6A, is configured as a region to be recorded. When the user selects the data display region recording 820, the data display region 410 of the data acquisition program screen 400, for example, as illustrated in FIG. 6B, is configured as a region to be recorded. When the user selects the model view region recording 830, the model view region 430 of the data acquisition program screen 400, for example, as illustrated in FIG. 6C, is configured as a region to be recorded. When the user selects the scanning region recording 860, the region 660 of the data acquisition program screen 400, for example, as illustrated in FIG. 6E, is configured as a region to be recorded.

When the user-designated region recording 840 is selected, the user may configure the location and size of the recording region, for example, as illustrated in FIG. 7.

When the pointer tracking recording 850 is selected, a region including a region corresponding to the location of the user input is configured as a region to be recorded, as illustrated in FIG. 6D. In an embodiment, a minimal region that includes both the region corresponding to the user input location (e.g., the pointer) and an additional region (e.g., the model view region) is configured as a region to be recorded. When the pointer tracking recording 850 is selected, an additional user interface (not shown) for selecting the region to be recorded (e.g., the model view region) along with the region corresponding to the user input location may be displayed.

Figure 9:
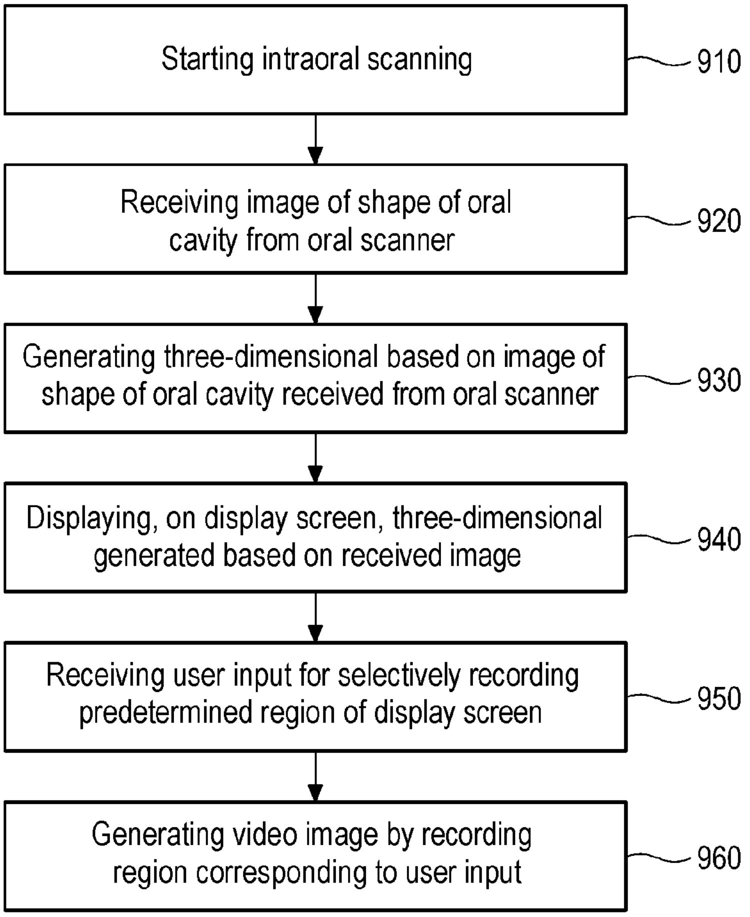
FIG. 9 illustrates a method of recording an oral cavity image according to various embodiments of the present disclosure.

FIG. 9 illustrates a method 900 of recording an oral cavity image according to various embodiments of the present disclosure. At least a part of the recording method according to the present disclosure may be a method implemented by a computer, such as the electronic device 100. Although steps of the method or algorithm according to the present disclosure have been illustrated in a sequential order in the illustrated flowchart, the steps may be performed in any order that allows the steps to be arbitrarily combined by the present disclosure, in addition to being performed sequentially. The description according to the present flowchart neither excludes making changes or modifications to the method or algorithm, nor implies that any step is essential or desirable. In an embodiment, at least some steps may be performed in parallel, iteratively, or heuristically. In an embodiment, at least some steps may be omitted, or other steps may be added.

In step 910, intraoral scanning using the oral scanner 200 is started. The oral scanner 200 may start scanning in response to an input using the input device 206 of the oral scanner 200, or in response to an input using a scan start interface 451 of the function option region 450 of the data acquisition program screen 400. The oral scanner 200 may transmit an image of a shape of a subject's oral cavity to the electronic device 100.

In step 920, the electronic device 100 receives the image of the shape of the oral cavity from the oral scanner 200 via the communication circuit 105 connected to the oral scanner 200. The received image may be a two-dimensional image.

In step 930, the electronic device 100 generates a three-dimensional image of the shape of the oral cavity based on the image of the shape of the oral cavity received from the oral scanner 200.

In step 940, the electronic device 100 displays the three-dimensional image generated based on the images received from the oral scanner 200 on a screen of the display 107. In an embodiment, the images regarding the shape of the oral cavity may be displayed on the data acquisition program screen 400. The data acquisition program screen may include a first screen region (e.g., the model view region 430) for displaying a three-dimensional image of the shape of the oral cavity, a second screen region (e.g., the live view region 420) for displaying a two-dimensional image of the shape of the oral cavity received from the oral scanner 200, and a third screen region (e.g., the function box region 440, the function option region 450, or the icon display region 460) for displaying an interface that provides functions for controlling the three-dimensional image of the shape of the oral cavity.

In step 950, the electronic device 100 receives a user input for selectively recording a predetermined region of the display screen, such as the data acquisition program screen 400. In the present embodiment, step 950 is illustrated as being performed subsequent to step 940. However, step 950 may be performed at any point in the oral cavity image recording method 900 illustrated in FIG. 9. In an embodiment, a screen region corresponding to the user input may include at least a portion of the first screen region for displaying a three-dimensional image of the shape of the oral cavity. In another embodiment, the screen region corresponding to the user input may include at least a portion of the first region and a least a portion of each of the second screen region for displaying a two-dimensional image of the shape of the oral cavity received from the oral scanner 200 and the third screen region for displaying an interface providing functions of processing, handling, and recording the three-dimensional image.

In step 960, in response to the user input for selectively recording a screen region, the electronic device 100 records a region corresponding to the user input to generate a video image. In an embodiment, a stored file may be stored in the memory 103 of the electronic device 100 and/or in a storage of a remote server.

In an embodiment, when the user input instructs selective recording of the first screen region, the electronic device 100 records a region that includes the first screen region but does not include the second screen region and the third screen region. In another embodiment, when the user input instructs selective recording of the first screen region and the second screen region, the electronic device 100 records a region that includes the first screen region and the second screen region but does not include the third screen region. In another embodiment, when the user input instructs recording of a screen region that includes at least one of the first, second, and third screen regions, the electronic device 100 records a region corresponding to the user input. When the user input instructs recording of the entire screen region, the electronic device 100 may record the entire screen region including the first, second, and third regions.

Figure 10:
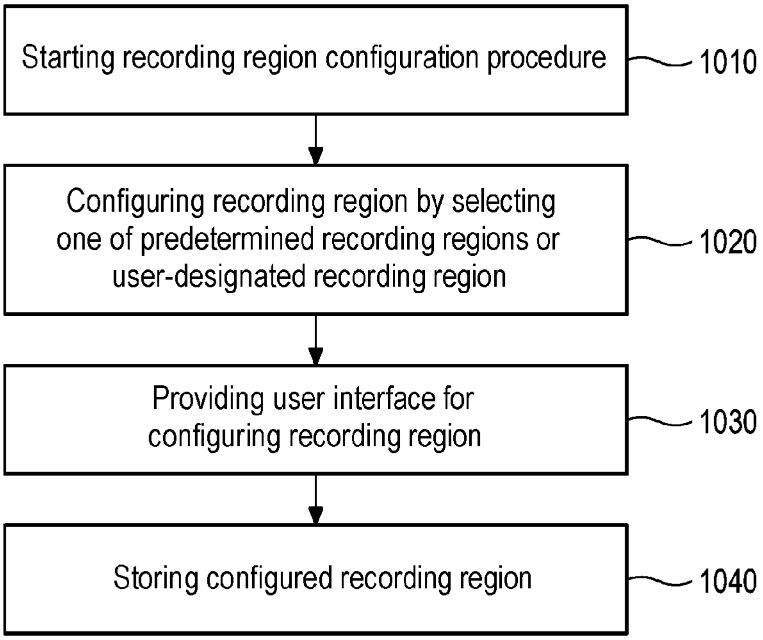
FIG. 10 illustrates a recording region configuration method according to various embodiments of the present disclosure.

FIG. 10 illustrates a recording region configuration method according to various embodiments of the present disclosure.

In step 1010, a procedure of configuring a recording region of the data acquisition program screen 400 is started. In an embodiment, the electronic device 100 may start the recording region configuration procedure in response to an input of selecting the recording region configuration icon 441 on the data acquisition program screen 400.

In step 1020, the electronic device 100 configures a recording region in response to an input of selecting one of predetermined recording regions, a user-designated recording region, or a pointer tracking recording region. The predetermined recording regions may include the entire region of the data acquisition program screen 400, the data display region 410, and the model view region 430.

When the user-designated recording region is selected, the electronic device 100 provides, in step 1030, a user interface for configuring the recording region. In an embodiment, the user may configure the recording region as illustrated in FIG. 7.

In step 1040, the electronic device 100 stores the configured recording region in the memory 103, etc.

Various embodiments of the present disclosure may be implemented as software recorded in a machine-readable recording medium. The software may be software for implementing the above-mentioned various embodiments of the present disclosure. The software may be inferred from various embodiments of the present disclosure by programmers in a technical field to which the present disclosure belongs. For example, the software may be a machine-readable command (e.g., code or a code segment) or program. A machine may be a device capable of operating according to an instruction called from the recording medium, and may be, for example, a computer. In an embodiment, the machine may be the device 100 according to embodiments of the present disclosure. In an embodiment, a processor of the machine may execute a called command to cause elements of the machine to perform a function corresponding to the command. In an embodiment, the processor may be the at least one processor 101 according to embodiments of the present disclosure. The recording medium may refer to any type of recording medium which stores data capable of being read by the machine. The recording medium may include, for example, ROM, RAM, a CD-ROM, a magnetic tape, a floppy disk, an optical data storage device, and the like. In an embodiment, the recording medium may be the at least one memory 103. In an embodiment, the recording medium may be distributed to computer systems which are connected to each other through a network. The software may be distributed, stored, and executed in the computer systems. The recording medium may be a non-transitory recording medium. The non-transitory recording medium refers to a tangible medium that exists irrespective of whether data is stored semi-permanently or temporarily, and does not include a transitorily transmitted signal.

Although the technical idea of the present disclosure has been described by the examples described in some embodiments and illustrated in the accompanying drawings, it should be noted that various substitutions, modifications, and changes can be made without departing from the technical scope of the present disclosure which can be understood by those skilled in the art to which the present disclosure pertains. In addition, it should be noted that such substitutions, modifications, and changes are intended to fall within the scope of the appended claims.

What is claimed is:

1. An electronic device comprising:

a communication circuit communicatively connected to a three-dimensional scanner;

an input device;

a display; and at least one processor, wherein the at least one processor is configured to:

generate a three-dimensional image of a shape of an oral cavity, based on an image acquired from the three-dimensional scanner via the communication circuit;

display, on the display, a screen comprising a first region in which at least the three-dimensional image is displayed;

receive a user input for selectively recording a predetermined region of the screen; and generate a video image by recording a region of the screen corresponding to the user input in response to the user input, wherein the recorded region comprises a portion of the first region, and wherein the electronic device detects a tooth in the image acquired from the three-dimensional scanner, starts recording a region corresponding to the user input in response to detecting the tooth, and stops recording when the tooth is not detected in the image acquired from the three-dimensional scanner for a predetermined time while recording the region corresponding to the user input.

2. The electronic device of claim 1, wherein the at least one processor is configured to display the screen further comprising a second region in which the image acquired from the three-dimensional scanner is displayed, and a third region in which an interface for controlling the three-dimensional image is displayed.

3. The electronic device of claim 2, wherein the at least one processor is configured to generate the video image by recording a region comprising the first region without including the second region and the third region in case that the user input instructs selective recording of the first region.

4. The electronic device of claim 2, wherein the at least one processor is configured to generate the video image by recording a region comprising the first region and the second region without including the third region in case that the user input instructs selective recording of the first region and the second region.

5. The electronic device of claim 2, wherein the at least one processor is configured to generate the video image by recording an entire region of the screen, which comprises the first region, the second region, and the third region, in case that the user input instructs full-screen recording.

6. The electronic device of claim 2, wherein the third region comprises a user interface for modifying and editing the three-dimensional image.

7. The electronic device of claim 1, wherein the user input is received via the input device of the electronic device.

8. The electronic device of claim 1, wherein the user input is received from the three-dimensional scanner via the communication circuit of the electronic device.

9. The electronic device of claim 8, wherein the user input is a gesture detected by a sensor module of the three-dimensional scanner.

10. A scan image processing method performed by an electronic device, which comprises at least one processor and at least one memory configured to store commands to be executed by the at least one processor, the method comprising:

generating a three-dimensional image of a shape of an oral cavity by the at least one processor based on an image acquired from a three-dimensional scanner;

displaying a screen comprising a first region on a display by the at least one processor, at least the three-dimensional image being displayed in the first region;

receiving, by the at least one processor, a user input for selectively recording a predetermined region of the screen; and generating, by the at least one processor, a video image by recording a region of the screen corresponding to the user input in response to the user input, wherein the recorded region comprises a portion of the first region, and wherein the scan image processing method further comprises:

detecting, by the at least one processor, a tooth in the image acquired from the three-dimensional scanner;

starting, by the at least one processor, recording a region corresponding to the user input in response to detecting the tooth, and stopping, by the at least one processor, recording when the tooth is not detected in the image acquired from the three-dimensional scanner for a predetermined time while recording the region corresponding to the user input.

11. The method of claim 10, wherein the at least one processor is configured to display, in the displaying, the screen further comprising a second region in which the image acquired from the three-dimensional scanner is displayed, and a third region in which an interface for controlling the three-dimensional image is displayed.

12. The method of claim 11, wherein the generating a video image by recording a region corresponding to the user input comprises generating the video image by recording a region comprising the first region without including the second region and the third region in case that the user input instructs selective recording of the first region.

13. The method of claim 11, wherein the generating a video image by recording a region corresponding to the user input comprises generating the video image by recording a region comprising the first region and the second region without including the third region in case that the user input instructs selective recording of the first region and the second region.

14. The method of claim 11, wherein the generating a video image by recording a region corresponding to the user input comprises generating the video image by recording an entire region of the screen, which comprises the first region, the second region, and the third region, in case that the user input instructs full-screen recording.

15. The method of claim 11, wherein the third region comprises a user interface for modifying and editing the three-dimensional image.

16. The method of claim 10, wherein the user input is received via an input device of the electronic device.

17. The method of claim 10, wherein the user input is received from the three-dimensional scanner.

18. The method of claim 17, wherein the user input is a gesture detected by a sensor module of the three-dimensional scanner.

19. A non-transitory computer-readable recording medium recording commands which, when executed by at least one processor, cause the at least one processor to perform an operation, wherein the commands cause the at least one processor to:

generate a three-dimensional image of a shape of an oral cavity based on an image acquired from a three-dimensional scanner;

display, on a display, a screen comprising a first region in which at least the three-dimensional image is displayed;

receive a user input for selectively recording a predetermined region of the screen; and generate a video image by recording a region of the screen corresponding to the user input in response to the user input, wherein the recorded region comprises a portion of the first region, and wherein the commands further cause the at least one processor to:

detect a tooth in the image acquired from the three-dimensional scanner;

start recording a region corresponding to the user input in response to detecting the tooth, and stop recording when the tooth is not detected in the image acquired from the three-dimensional scanner for a predetermined time while recording the region corresponding to the user input.

20. A system for three-dimensional scanning, comprising:

a three-dimensional scanner comprising an input device and configured to scan a shape of an oral cavity; and an electronic device communicably coupled to the three-dimensional scanner, wherein the electronic device comprises:

a communication circuit communicatively connected to the three-dimensional scanner;

an input device;

a display; and at least one processor, wherein the at least one processor is configured to:

generate a three-dimensional image of the shape of the oral cavity based on an image acquired from the three-dimensional scanner via the communication circuit;

display, on the display, a screen comprising a first region in which at least the three-dimensional image is displayed;

receive a user input for selectively recording a predetermined region of the screen; and generate a video image by recording a region of the screen corresponding to the user input in response to the user input, wherein the recorded region comprises a portion of the first region, and wherein the electronic device detects a tooth in the image acquired from the three-dimensional scanner, starts recording a region corresponding to the user input in response to detecting the tooth, and stops recording when the tooth is not detected in the image acquired from the three-dimensional scanner for a predetermined time while recording the region corresponding to the user input.

21. The system of claim 20, wherein the three-dimensional scanner is configured to receive a start input via the input device of the three-dimensional scanner, and wherein the electronic device starts recording of a region corresponding to the user input in response to the start input received from the three-dimensional scanner via the communication circuit.

* * * * *